United States Patent [19]

Anzenberger, Sr.

[11] Patent Number: 4,477,572

[45] Date of Patent: Oct. 16, 1984

[54] REMOTE MONITORING OF ESTER FUNCTIONAL FLUIDS

[75] Inventor: Joseph F. Anzenberger, Sr., New City, N.Y.

[73] Assignee: Stauffer Chemical Company, Westport, Conn.

[21] Appl. No.: 383,361

[22] Filed: May 28, 1982

[51] Int. Cl.$^3$ .................. G01N 27/02; G01N 27/04
[52] U.S. Cl. ........................... 436/6; 436/60; 436/150; 324/65 CR; 204/1 T
[58] Field of Search ............... 436/6, 34, 128, 60, 436/150; 204/1 T, 1 K, 1 C, 400; 324/65 CR; 338/13; 73/61.2, 83, 86

[56] References Cited

U.S. PATENT DOCUMENTS

| | | | |
|---|---|---|---|
| 2,987,685 | 6/1961 | Schaschl | 338/13 X |
| 2,991,439 | 7/1961 | Marsh et al. | 338/13 |
| 3,073,154 | 1/1963 | Schaschl et al. | 73/86 |
| 3,209,296 | 9/1965 | Seffens et al. | 338/13 |
| 4,029,554 | 6/1977 | Ellison | 204/1 T |

Primary Examiner—Robert Yoncoskie
Attorney, Agent, or Firm—Roger S. Benjamin

[57] ABSTRACT

The degradation of a hydrolyzable ester containing functional fluid is monitored by placing in the fluid a probe-containing a corrodible metal sensor and measuring by electrical means the corrosion of the sensor.

11 Claims, 2 Drawing Figures

REMOTE MONITORING OF ESTER FUNCTIONAL FLUIDS

BACKGROUND OF THE INVENTION

The prior art teaches the use of test probes in chemical process environments. Some prior art probes use metals as electrodes in a galvanic cell. In other probes an active metal portion of the probe is corroded and its decrease in cross-sectional area is used as an indicator of the corrosivity of its environment. U.S. Pat. Nos. 2,735,754; 2,851,570; 2,987,685; 2,991,439; 2,994,219; 3,004,232; 3,060,721; 3,073,154; 3,108,242, and 3,124,771 show test probes having corrodible metal sensors and electrical resistance measuring systems for their use. The technical advance of most prior art probes resides in the arrangement of probe parts or in the designing of the electrical circuit which detects minute levels of test probe metal loss.

U.S. Pat. No. 4,029,554 discusses oxidative acid buildup in synthetic lubricating oils and uses conventional titration tests for determining acidity. This patent measures electromotive force in a battery formed of dissimilar metals to gauge the degree of synthetic oil degradation.

The prior art corrodible sensor probes do not distinguish between corrosion problems associated with different classes of functional fluids. For example, petroleum lubricants may degrade by an oxidative mechanism, whereas certain synthetic fluids such as organic esters and organophosphates are susceptable to hydrolysis and acid release.

The acidity developed by hydrolyzable ester functional fluids is conventionally measured by wet analysis methods—viz., acid number by alkali titration. Unfortunately the routine taking of aliquot samples for acid number determination is costly, inconvenient, or hazardous for some industrial applications.

A need exists for a simple remote monitoring system adapted to detect the degradation of modern synthetic hydrolyzable ester functional fluids.

FIELD OF THE INVENTION

This invention is a method of operating with hydrolyzable ester functional fluids to detect fluid corrosive potential remotely.

THE INVENTION

This invention is an improved method for remotely monitoring the degradation of hydrolyzable ester fluids, wherein a test probe containing a corrodible metal sensor is placed in the fluid and corrosion of the sensor is monitored by electrical means. Moreover, this invention is a method of lubricating the moving parts of a machine using the remote monitoring method of this invention.

DETAILED DESCRIPTION OF THE INVENTION

Figure 2:
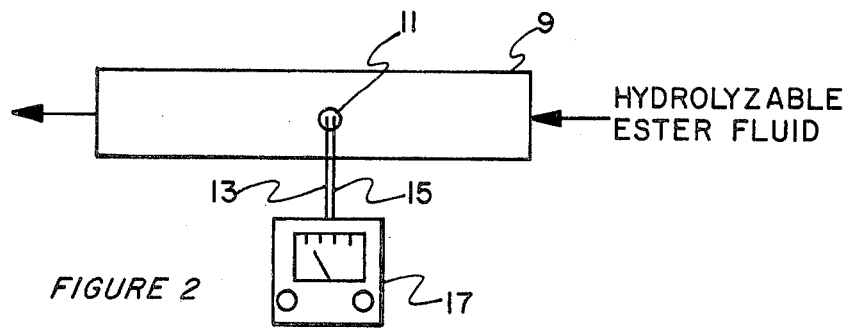
FIG. 2 is a perspective view of an electrically metered test probe inserted in a conduit carrying functional fluid.

Hydrolyzable ester functional fluids have general utility for applications such as lubricants, heat exchange media, and hydraulic fluids. Particularly desirable functional fluids are synthetic esters characterized as ISO VG 32 or ISO VG 46 selected from the classes of organic esters and triorganophosphates. These classes of esters have advantageous properties of high temperature operation and resistance to degradation.

Organic ester oils are prepared as the reaction product of organic acids and alcohols. One group of useful organic esters are derived from the reaction of dicarboxylic acids and monohydric alcohols. Typical polycarboxylic acids suitable for forming such esters are sebacic acid, adipic acid, and azelaic acid. Suitable monohydric alcohols are alcohols having from six to eighteen carbon atoms.

A second group of useful organic ester oils are derived from the reaction product of polyhydric alcohols and monocarboxylic acids. Examples of suitable polyhydric alcohols are trimethylolpropane, glycerol, pentaerythritol, and dipentaerythritol. Suitable acids for ester formation are monocarboxylic acids having six to thirty carbon atoms. Organic ester oils have degradation products which include potentially corrosive carboxylic acids.

Another class of ester functional fluids to which this invention is applicable are the triorganophosphates represented by the formula:

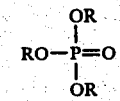

wherein the R groups are the same or different and are selected from alkyl, aryl, aralkyl, and alkaryl groups having from one to twenty carbon atoms. Suitable triaryl phosphates include; cresyl phosphates, xylyl phosphates, isopropylphenyl/phenyl phosphates, secondarybutylphenyl/phenyl phosphates, tertiarybutylphenyl/phenyl phosphates, isodecyl/phenyl phosphates, 2-ethylhexyl/phenyl phosphates, and tributylphosphate. Particularly preferred phosphate esters are tertiarybutylphenyl/diphenyl phosphate, ditertiarybutylphenyl/phenyl phosphate, or triorganophosphate mixtures containing at least fifty weight percent of these tertiarybutyl phenyl/phenyl phosphate esters. Phosphate esters are known to degrade by hydrolysis to give acids. For example, hydrolytic degradation of triaryl phosphates may form diphenyl acid phosphates.

This invention is also applicable to mixtures of organic esters and triorganophosphates. Moreover, this invention is useful for determining the condition of functional fluids having at least about one-third by weight of their composition comprising organic ester or triorganophosphate.

The process of the invention is carried out by inserting into the working environment of a functional fluid a test probe having a corrodible metal sensor. "Corrosion" of the metal sensor is a term describing a chemical change wherein the metal comprising the sensor passes from an elementary to a chemically combined state. The effect of metal sensor corrosion is to change the sensor from an electrically conductive to a comparatively non-conductive condition. For example, a metal sensor may display a resistance of less than 1000 ohms when intact and a resistance in excess of 10,000 ohms when completely corroded.

The metal sensor portion of the probe is composed of a corrodible metal selected from a metal or alloy having a standard electrode potential of less than −0.13 volts. Standard electrode potential of the electromotive series of elements as defined for this invention is set out in Table 22-1, pgs. 541-543 of *College Chemistry with Qualitative Analysis*, 5th edition, (1972) D. C. Heath and Co. Publ, ISBN 0-669-91355-3; the disclosure of which is incorporated herein by reference. Specific metals having utility in this invention are iron, zinc, magnesium, calcium, sodium, potassium, and alloys thereof. Moreover, these metals and their alloys may be further alloyed with other less active metals provided that the resultant alloy has a standard electrode potential less than −0.13 volts. For example, sodium may be alloyed with lead to give a corrodible alloy suitable for use as a metal sensor. The preferred metal sensor of this invention is zinc.

The dimensions of the active metal sensor are not critical to the practice of the invention. The corrodible metal sensor may be in the shape of a wire, bar, coil, plate, or set of plates. A sensor having a cross-sectional area of from about 0.005 mm$^2$ to about 0.1 mm$^2$ is particularly suitable. The length of the metal sensor is not critical but may conveniently vary from about one to about fifty millimeters.

The metal sensor is attached to conductive leads which are not readily corroded by the functional fluid environment. The leads may be made of platinum, gold, silver, copper alloy, or stainless steel.

The sensor and its associated leads are mounted in a probe assembly. The probe assembly has a configuration suitable for positioning the sensor and leads in a functional fluid environment. Moreover, the probe provides means for supporting and positioning the sensor leads in an insulating and sealing medium. The probe construction provides sealing to prevent leakage of the fluid through the probe. In addition, the probe construction has an insulated support for the sensor leads to enable electrical connection of the leads to an external electrical monitoring means.

A probe assembly and its placement during use are shown in the drawing.

Figure 1:
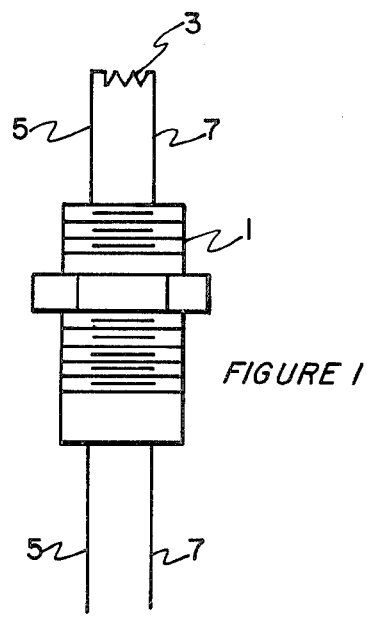
FIG. 1 is a side view of a test probe assembly.

FIG. 1 illustrates a probe assembly having a threaded body member (1). The interior of the body member (1) contains a fluid sealing plastic insulator which supports leads (5) and (7). The leads (5) and (7) are electrically attached to the zinc metal sensor (3).

FIG. 2 depicts a conduit (9) carrying a hydrolyzable ester fluid. A probe (11) similar in construction to the probe of FIG. 1 is mounted in the wall of conduit (9). External electrical leads (13) and (15) from the external portion of the probe are connected to remote electric resistance meter (17) to monitor the condition of the fluid in the conduit.

The electrical monitoring means may measure resistance (DC) or impedance (AC). The impedance may be inductive, for example, a metal sensor in the form of a coil whose inductive properties are changed by corrosion. Again, the impedance may be capacitive, for example a metal sensor in the form of metal plates, whose capacitive properties are changed by corrosion. Still again, the impedance may be resistive, for example, a wire whose resistive properties vary in proportion to corrosion. If desired, the electrical means may monitor corrosion by measuring changes in any combination of impedance properties.

A preferred embodiment of the invention is to measure electrical resistance (or reciprocal resistance) of the metal sensor. Resistance measurement may be measured by a variety of conventional electrical instruThis invention uses as a particularly preferred embodiment electrical monitoring means which measure only gross changes in resistance. Corrosion of the sensor is detected by an open/closed circuit indicator.

A plurality of sensors may be used in the process of monitoring the corrosivity of the hydrolyzable ester functional fluid. A probe may contain one or more metal sensors. For example, a probe may contain zinc wires of different diameters. Alternatively, the probe may contain sensors composed of different metals. Thus, a zinc and magnesium sensor may be independently used in the same probe assembly.

Multiple metal sensors (and attached leads) may be connected in a parallel or series circuit. If desired, each metal sensor may be electrically independent.

The method of this invention includes the use of a plurality of probes. A preferred embodiment of the invention employs a plurality of independent metal sensors of different cross-sectional area. The sequential formation of an open circuit for each sensor will serve to monitor the successive degradation of the fluid.

The extent of corrosion of the metal sensor will increase with increasing acid number. The functional relationship between the variables of acid number and sensor resistance/impedance may be determined by routine experimentation for a probe of any desired composition.

A functional fluid determined by the method of this invention to have unacceptable corrosive potential is replaced or withdrawn for treatment. Treatment of the used fluid to reduce its corrosivity may be accomplished by conventional methods such as chemical treatment, filtering, distillative fractionation, or dilution.

The invention has particular utility in monitoring the condition of hydrolyzable ester fluids used in hazardous locations. For example, phosphate ester functional fluids used in the proximity of nuclear reactors may be monitored by the process of this invention without the necessity of taking fluid samples prior to fluid replacement.

The following examples illustrates the process of the invention.

EXAMPLE I

A three neck 1000 milliliter round bottom flask was equipped with a heating jacket, thermostatic control, stirrer blade, water-cooled reflux tube, and corrodible probe assembly.

792 grams of Fyrquel ®GT (brand of tertiarybutylphenyl/phenyl phosphate, product of Stauffer Chemical Company) were charged to the flask together with 8 grams of water. The stirring rod had attached to it a copper coupon. The 1% water charge and copper coupon were used to promote degradation of the ester fluid.

The contents of the flask were heated to 93.3° C., and the motor driven stirrer operated to provide vigorous stirring. Vapor from the stirred and heated fluid was cooled and returned to the flask as liquid by the water-cooled condenser tube. During the test procedure the volume of the flask content remained substantially constant. The corrosion probe assembly comprised a gold plated threaded cylindrical plug containing a plastic insulator in its interior. The insulator supported a zinc wire sensor and attached conductive leads. The leads exiting the probe were electrically connected to a bridge type electrical meter which permitted measurement of relative resistivity.

The condition of the ester fluid was periodically monitored by determination of its acid number.

The experimental results are set out in Table I.

TABLE I

| Day Number | Time 24 hr. Scale | Temp °C. | Cumulative hrs. at 93.3° C. | Relative Resistivity of Zinc Wire(Diameter) | | Acid No. Mg KOH/gm[3] |
|---|---|---|---|---|---|---|
| | | | | .1778 mm. | .2286 mm. | |
| 1 | 10:30 | 93.3 | 0 | 0 | 0 | |
| 2 | 16:30 | 93.3 | 30 | 0 | 0 | 0.067 |
| 3 | 8:30 | 93.3 | 46 | 0 | 0 | |
| 3 | 10:30 | 93.3 | 48 | 0 | 0 | 0.070 |
| 3 | 16:30 | 93.3 | 54 | 0 | 0 | |
| 7 | 8:30 | RT[2] | 54 | 0 | 0 | |
| 7 | 10:15 | 93.3 | 54 | 0 | 0 | 0.073 |
| 7 | 14:30 | 93.3 | 58 | 0 | 0 | |
| 7 | 16:30 | 93.3 | 60 | 0 | 0 | |
| 8 | 8:30 | 93.3 | 76 | 0 | 0 | 0.367 |
| 8 | 13:00 | 93.3 | — | 0 | 0 | |
| 8 | 14:30 | 93.3 | 82 | 0 | 0 | 0.433 |
| 8 | 16:30 | 93.3 | 84 | 0 | 0 | 0.465 |
| 9 | 8:30 | RT | 84 | 0 | 0 | |
| 9 | 9:00 | 87.8 | 84 | 0 | 0 | |
| 9 | 10:30 | 93.3 | 86 | 0 | 0 | |
| 9 | 11:30 | 93.3 | 87 | 0 | 0 | 0.490 |
| 9 | 11:34 | 93.3 | 87 | 95 | 0 | |
| 9 | 13:00 | 98.9 | 87+ | ∞ | 0 | |
| 9 | 13:30 | 93.3 | 88 | ∞ | 0 | 0.570 |
| 9 | 15:00 | 93.3 | 90 | ∞ | 0 | |
| 9 | 16:30 | 93.3 | 92 | ∞ | 0 | |
| 10 | 8:20 | RT | 92 | ∞ | 0 | |
| 10 | 9:00 | 93.3 | 92 | ∞ | 0 | |
| 10 | 9:02 | 93.3 | 92+ | ∞ | 100 | 0.929 |

[1]Relative Resistivity: 0 is closed circuit, other numerical values indicate appreciable reduction in sensor cross sectional area; ∞ is open circuit, fully corroded sensor wire.
[2]room temperature
[3]ASTM D 974 - Neutralization number by color indicator titration.

EXAMPLE II

The apparatus and test condition of Example I were employed for this test. 800 grams of Basestock 704, TM brand lubricant, triheptanoic ester of trimethylol propane, product of Stauffer Chemical Company, were charged to the 1000 ml flask with 9 grams of distilled water. A test probe equipped with a (0.009 inch) 0.2286 mm. zinc wire was used as the metal sensor. Experimental results are shown in Table II below:

TABLE II

| Day | Temp °C. | Hours | Acid No. Mg. KOH/gm | Relative Resistance |
|---|---|---|---|---|
| 1 | 93.3 | 0 | 0.026 | 0 |
| 2 | " | 24 | 0.086 | 0 |
| 3 | " | 48 | 0.191 | 0 |
| 4 | " | 72 | 0.302 | 0 |
| 5 | " | 96 | 0.519 | 0 |
| 10 | " | 120 | 0.758 | 0 |
| 11 | " | 147 | 1.224 | 0 |
| 12 | " | 168 | 1.738 | 0 |
| 15 | " | 175 | 2.119 | ∞ |

The foregoing description of the invention has been presented describing certain operable and preferred embodiments. It is not intended that the invention should be so limited since variations and modifications thereof will be obvious to those skilled in the art, all of which are within the spirit and scope of this invention.

I claim:

1. A method of remotely monitoring the degradation of hydrolyzable ester containing functional fluid which comprises placing in said fluid at least one probe containing at least one corrodible metal sensor, said metal sensor having a standard electrode potential of less than −0.13 volts, and measuring by electrical means the corrosion of said metal sensor in said fluid.

2. The method of claim 1 wherein the fluid contains at least one-third of a hydrolyzable ester selected from the group consisting of organic ester derived from the reaction of polycarboxylic acid with an alcohol, organic ester derived from the reaction of monocarboxylic acid with polyhyric alcohol, triorganophosphate, and mixtures thereof.

3. The method of claim 2 wherein said triorganophosphate is represented by the formula;

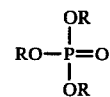

wherein the R groups are the same or different and are selected from alkyl, aryl, alkaryl, and aralkyl groups having from one to twenty carbon atoms.

4. The method of claim 3 wherein said triorganophosphate contains R groups comprising aryl or alkaryl or mixtures thereof.

5. The method of claim 3 wherein the triaryl phosphate is a tertiarybutylphenyl/phenyl phosphate.

6. The method of claim 1 wherein the metal sensor comprises iron, magnesium, zinc, calcium, sodium, potassium or alloys thereof.

7. The method of claim 1 wherein the metal sensor comprises zinc.

8. The method of claim 1 wherein said functional fluid is monitored with a plurality of probes.

9. The method of claim 1 wherein said functional fluid is monitored with a plurality of metal sensors.

10. The method of claim 1 wherein said electrical means monitors oxidation of the sensor by measuring electrical resistance.

11. The method of claim 1 wherein the electrical means monitors oxidation of the sensor by measuring electrical impedance.

* * * * *

UNITED STATES PATENT AND TRADEMARK OFFICE
CERTIFICATE OF CORRECTION

PATENT NO. : 4,477,572

DATED : October 16, 1984

INVENTOR(S) : Joseph F. Anzenberger, Sr.

It is certified that error appears in the above—identified patent and that said Letters Patent is hereby corrected as shown below:

Col. 1, line 31, "susceptable" should be -- susceptible --;

Col. 1, line 32, "ard" should be -- and --;

Col. 2, line 39, "phosphatcs" should be -- phosphates --;

Col. 4, line 1, "electrical instruThis" should read -- electrical instruments such as a Wheatstone bridge or a Kelvin bridge. This -- ;

Col. 4, line 4, "de" after "is" should read -- de- --; and

Col. 6, line 51, "mixtures thereof:" should read -- mixtures thereof. --.

Signed and Sealed this

Twenty-fifth Day of June 1985

[SEAL]

Attest:

DONALD J. QUIGG

Attesting Officer

Acting Commissioner of Patents and Trademarks